United States Patent
Pelc et al.

(10) Patent No.: US 8,509,380 B2
(45) Date of Patent: Aug. 13, 2013

(54) INVERSE GEOMETRY VOLUME COMPUTED TOMOGRAPHY SYSTEMS

(75) Inventors: Norbert Joseph Pelc, Los Altos, CA (US); Tobias Funk, Martinez, CA (US); Joseph Anthony Heanue, Oakland, CA (US); Waldo Stephen Hinshaw, Burlingame, CA (US); Edward Gerald Solomon, Menlo Park, CA (US); Brian Patrick Wilfley, Los Altos, CA (US)

(73) Assignees: The Board of Trustees of the Leland Stanford Junior University, Palo Alto, CA (US); Triple Ring Technologies, Inc., Newark, CA (US)

( * ) Notice: Subject to any disclaimer, the term of this patent is extended or adjusted under 35 U.S.C. 154(b) by 328 days.

(21) Appl. No.: 13/052,020

(22) Filed: Mar. 18, 2011

(65) Prior Publication Data

US 2011/0228898 A1     Sep. 22, 2011

Related U.S. Application Data

(60) Provisional application No. 61/315,780, filed on Mar. 19, 2010.

(51) Int. Cl.
*A61B 6/00*     (2006.01)

(52) U.S. Cl.
USPC ............................................................ 378/9

(58) Field of Classification Search
USPC ........................................... 378/4–20
See application file for complete search history.

(56) References Cited

U.S. PATENT DOCUMENTS

| | | | |
|---|---|---|---|
| 4,274,005 A * | 6/1981 | Yamamura et al. | 378/9 |
| 7,233,644 B1 * | 6/2007 | Bendahan et al. | 378/57 |

* cited by examiner

*Primary Examiner* — Courtney Thomas
(74) *Attorney, Agent, or Firm* — Joseph T. Lin

(57) ABSTRACT

The present invention pertains to an apparatus and method for inverse geometry volume computed tomography medical imaging of a human patient. A plurality of x-ray sources for producing x-ray radiation are used. The gaps between the x-ray sources is less than 20 cm. A collimator located between the plurality of x-ray sources and the human patient is also used. A detector is also used.

7 Claims, 16 Drawing Sheets

INVERSE GEOMETRY VOLUME COMPUTED TOMOGRAPHY SYSTEMS

RELATED U.S. APPLICATION

This application claims priority to the U.S. provisional patent application Ser. No. 61/315,780, entitled "Inverse Geometry Volume Computed Tomography Systems," with filing date Mar. 19, 2010.

STATEMENT REGARDING FEDERALLY SPONSORED RESEARCH

This invention was made with government support under Contract EB006837 awarded by the National Institute of Health. The government has certain rights in the invention.

BACKGROUND

Modern computed tomography (CT) scanners have the goal of covering a large volume of the patient in a single rotation at very fast rotation speeds. This objective is driven by demands of cardiac CT to cover the entire organ in less than a heartbeat. Impressive results have been achieved with the current generation of CT scanners. However, the downside of this development is the increased dose to the patient, the increase in scatter, and the degradation of image quality in the outer slices due to cone beam artifacts. In particular, the increased dose in medical imaging has come under scrutiny, with several published studies documenting the elevated risk of cancer resulting from the radiation involved in medical imaging.

The manufacturers of CT scanners are attempting to address dosage concerns with new developments. One common avenue being pursued is the use of photon counting detectors. Photon counting detectors have intrinsically higher detective quantum efficiency (DQE) than integrating detectors and have a bias towards lower photon energies. These qualities lead to increased image contrast, resulting in lower dose while maintaining image quality. Even more contrast enhancement and dose reduction can be achieved with the use of energy-resolving detectors. However, photon counting and energy resolving detectors are significantly more expensive than integrating detectors. This increased cost is particularly challenging for conventional CT scanners that rely on detectors with very large areas.

CT manufacturers are exploring a variety of other methods to reduce this dose while maintaining image quality. However, these improvements are expected to be minor compared to that which may be gained by an alternative CT system concept, inverse-geometry CT (IGCT). Conventional CT utilizes a single focal spot X-ray source and a large-area detector, whereas IGCT utilizes a large-area, multi-focal spot X-ray source and a small-area detector. IGCT offers higher dose efficiency and faster acquisition times than state-of-the-art conventional CT systems. Thus, IGCT has the potential to overcome disadvantages with conventional CT and significantly out-perform conventional CT scanners.

In conventional CT scanners, each projection is of the entire field of view and is obtained with a single focal-spot X-ray source and a large detector. By contrast, inverse geometry systems utilize a large-area scanned X-ray source and a field-of-view projection is composed of many narrower projections each acquired with a different detector location. The detector in an IGCT system is quite small compared to that in a conventional CT system. Thus, it is economically feasible to implement advanced yet more expensive detector technologies in IGCT. However, IGCT faces difficulties in implementation due to a large source array to be rotated at high speeds and significant challenges from high power and cooling requirements of the source.

What is needed is a CT imaging system capable of producing rapid high quality images. Furthermore, the CT imaging system should reduce the effects of cone beam artifacts.

SUMMARY

The present invention pertains to an apparatus and method for computed tomography medical imaging of a human patient. A plurality of x-ray sources for producing x-ray radiation are used. The gaps between the x-ray sources is less than 20 cm. The gaps can be angled, chevron shaped or other shape. A collimator located between the plurality of x-ray sources and the human patient is used for projecting the x-ray radiation through the human patient. A x-ray detector is used for measuring amount of the x-ray radiation passing through the human patient and striking the detector.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

Figure 1:
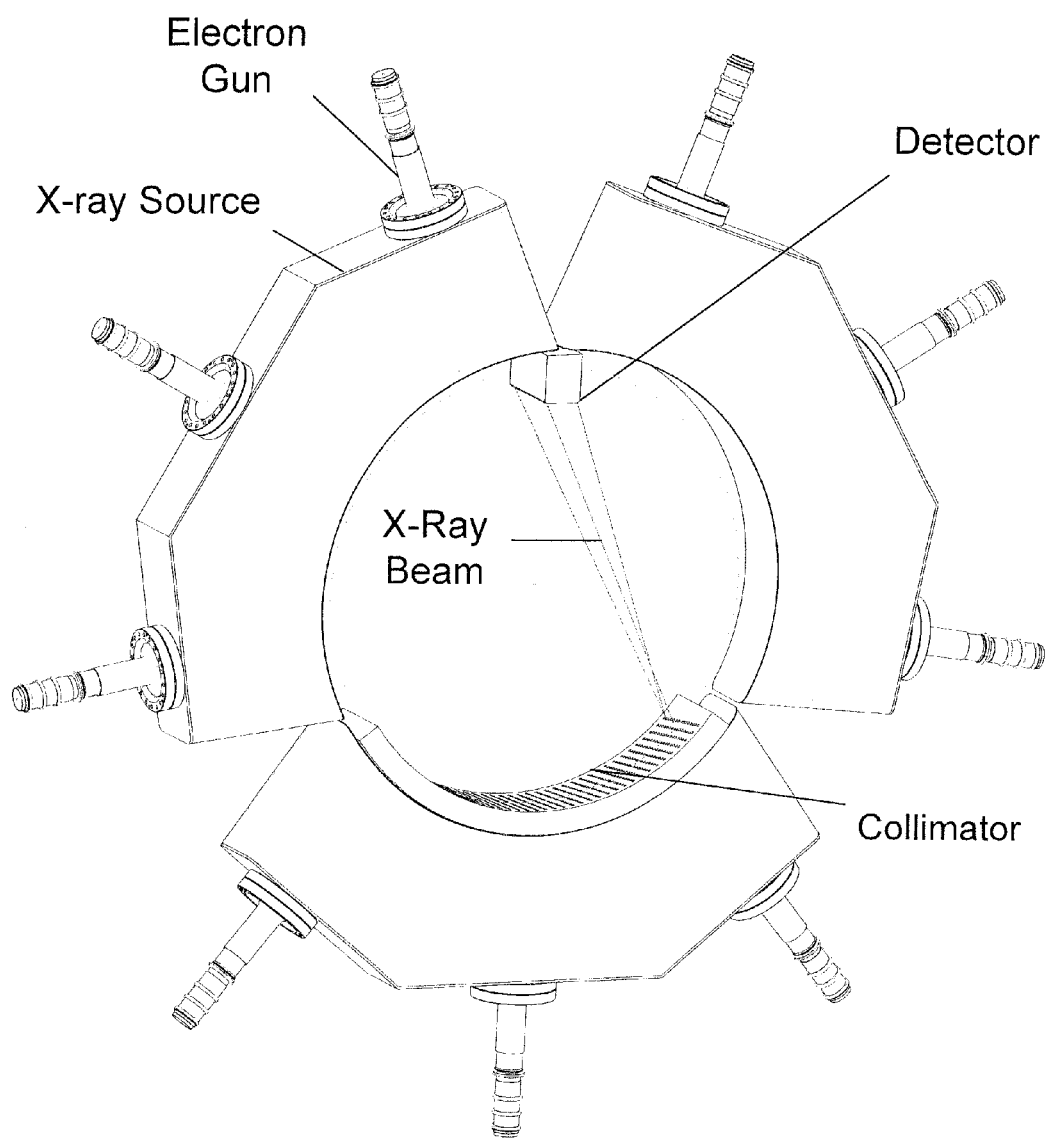
FIG. 1 is a diagram showing an exemplary computed tomography imaging system of one embodiment of the present invention with three vacuum envelopes.

FIG. 1 is a diagram showing an exemplary computed tomography imaging system of one embodiment of the present invention. Imaging system 100 comprises a ring of X-ray sources 101, 102, and 103. The source ring can be made of three X-ray sources 101, 102, and 103 making a three-gap system as shown. For the three-gap system, there can be three separate source arrays, each containing three electron guns in a single vacuum envelope. The source-spot locations can cover the full 360 degrees, except for a small gap of a few centimeters between each of these arrays. Imaging system 100 can have a large ring of scanning X-ray source-spots. Inside the source-ring can be detectors and collimators. The detector elements can be read after each opposing source-spot fires.

Figure 2:
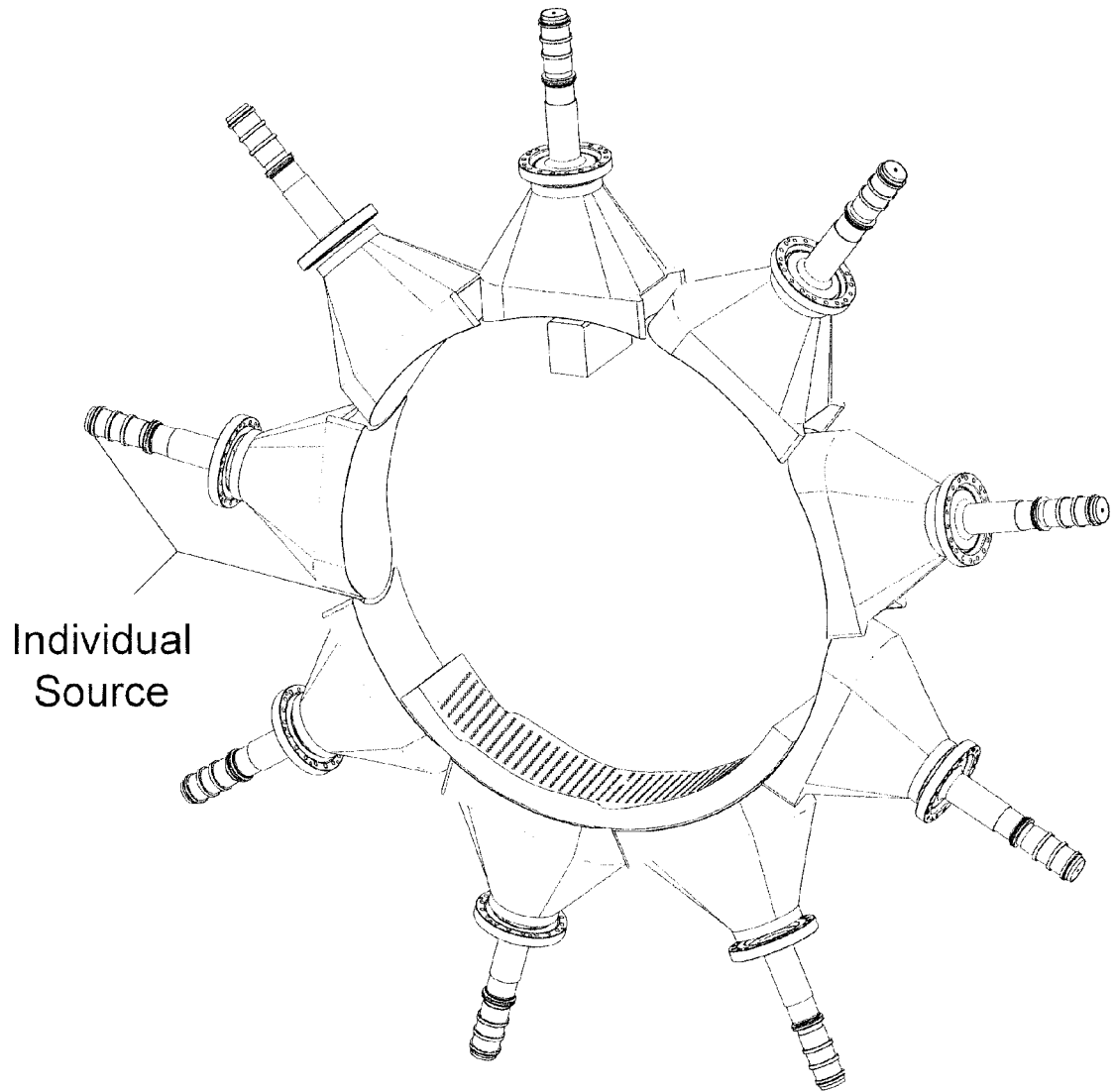
FIG. 2 is a diagram showing an exemplary computed tomography imaging system of one embodiment of the present invention with nine vacuum envelopes.

FIG. 2 is a diagram showing an exemplary computed tomography imaging system of one embodiment of the present invention with nine vacuum envelopes. In this embodiment, the source ring is made from nine individual X-ray sources forming a nine-gap system. There are nine separate source arrays, each containing a single electron gun in a single vacuum envelope.

Figure 3:
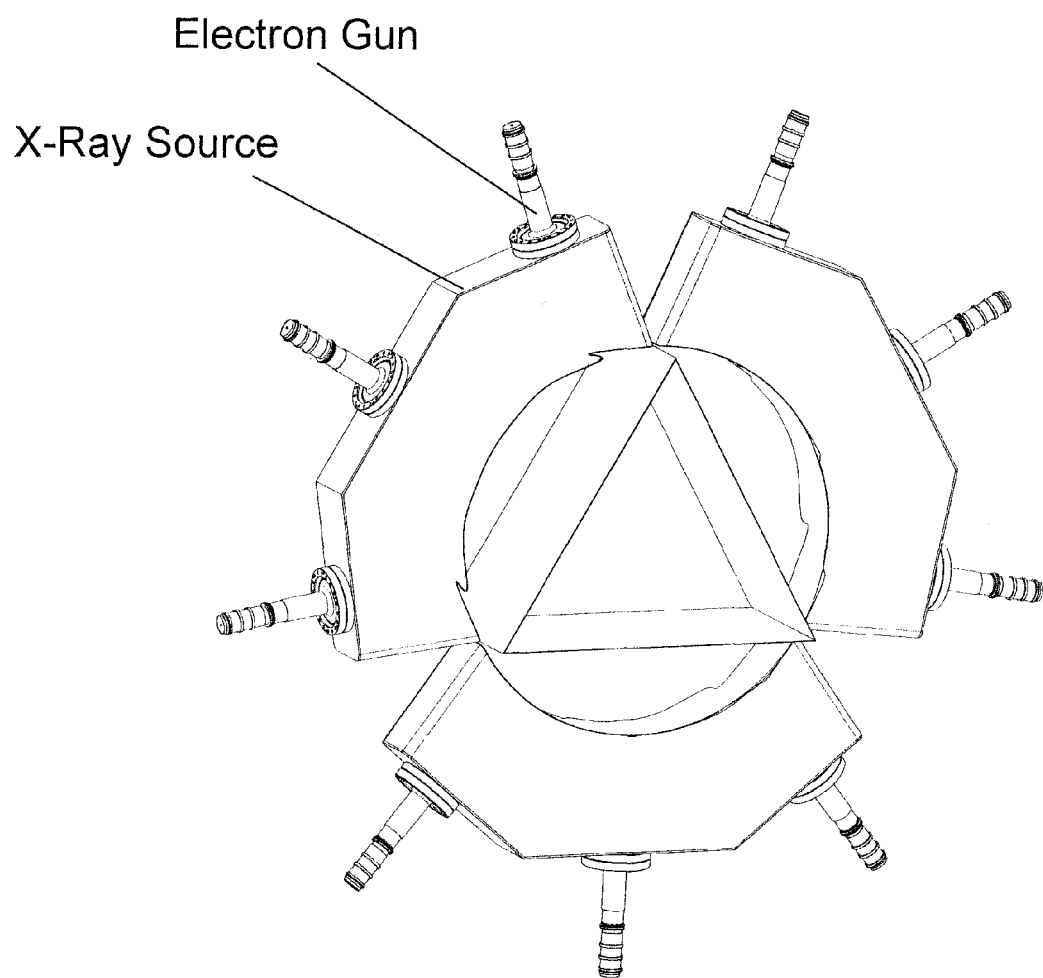
FIG. 3 is a diagram showing three vacuum envelopes arranged to form only three gaps for sample completeness within a volume described by a triangle.

FIG. 3 is a diagram showing three vacuum envelopes arranged to form only three gaps for sample completeness within a volume described by a triangle. An important requirement is to achieve complete sampling of the object. One obvious advantage of imaging system 100 is that the sources and detector extend over the full z-range of the object. In cone-beam CT, this is not the case as it uses only a single focal spot X-ray tube. This leads to under-sampling of the object in the z direction and is responsible for cone-beam artifacts.

An ideal CT scanner comprises a ring of X-ray sources without any gaps in coverage. However, in a realistic system the source ring comprises individual X-ray tubes resulting in gaps in source coverage. For the three-gap system, a two-dimensional Radon space analysis can be sufficient. Sampling is complete within the field of view. In this case, extension to the three-dimensional case is straight forward as sampling is complete on a slice-by-slice basis.

As discussed earlier, the system design for imaging system 100 can be simplified by using nine tubes with individual vacuum envelopes and gaps in between. However, in this case the two-dimensional analysis reveals missing data in Radon space that could lead to artifacts in the reconstruction if the gaps are not configured properly. The gaps between the tubes can be designed in a way that neighboring slices fill in the missing data thereby producing complete sampling.

Figure 4:
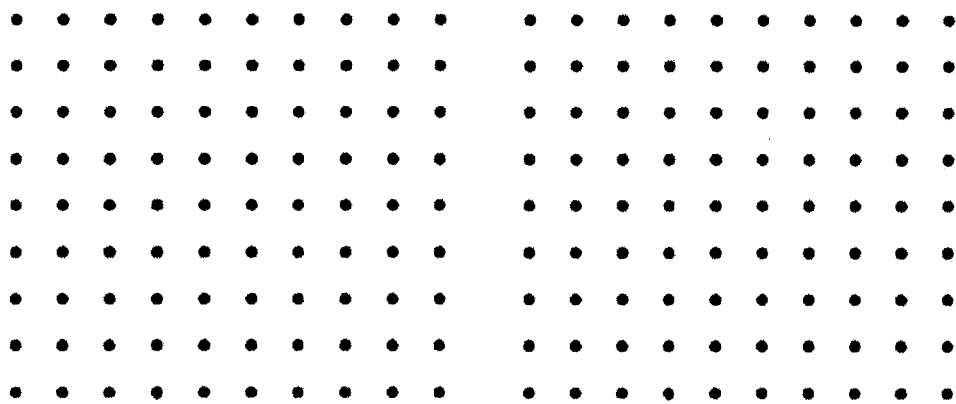
FIG. 4 is a diagram showing source positions with a straight gap between adjacent tubes or vacuum envelopes.
Figure 5:
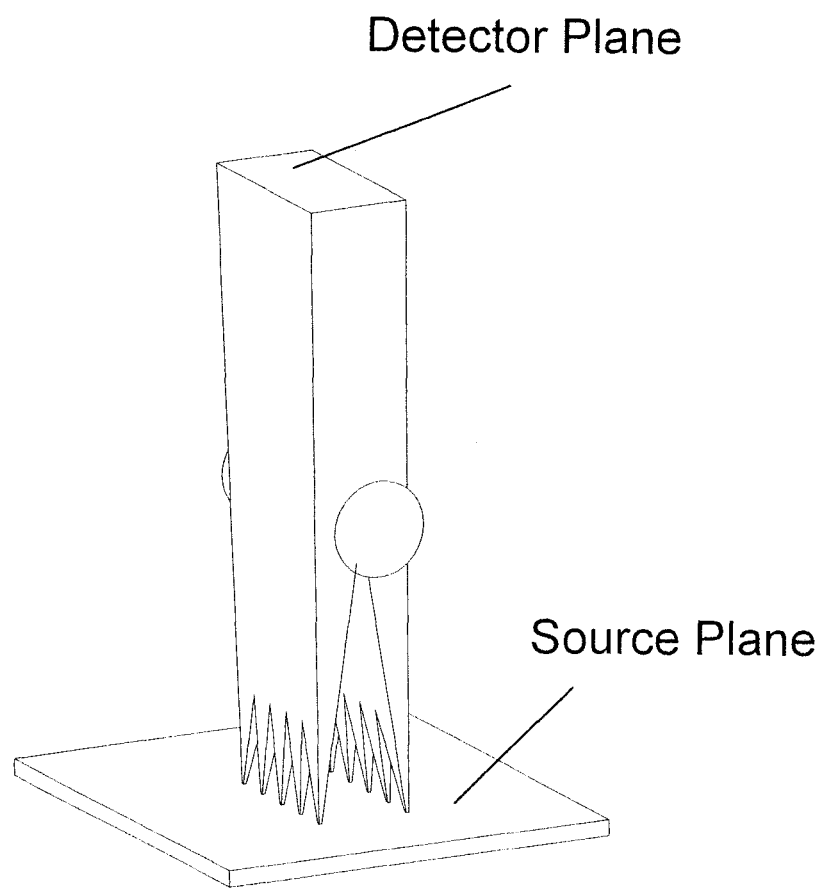
FIG. 5 is a diagram showing a cylinder penetrated by beams with a straight gap.
Figure 6:
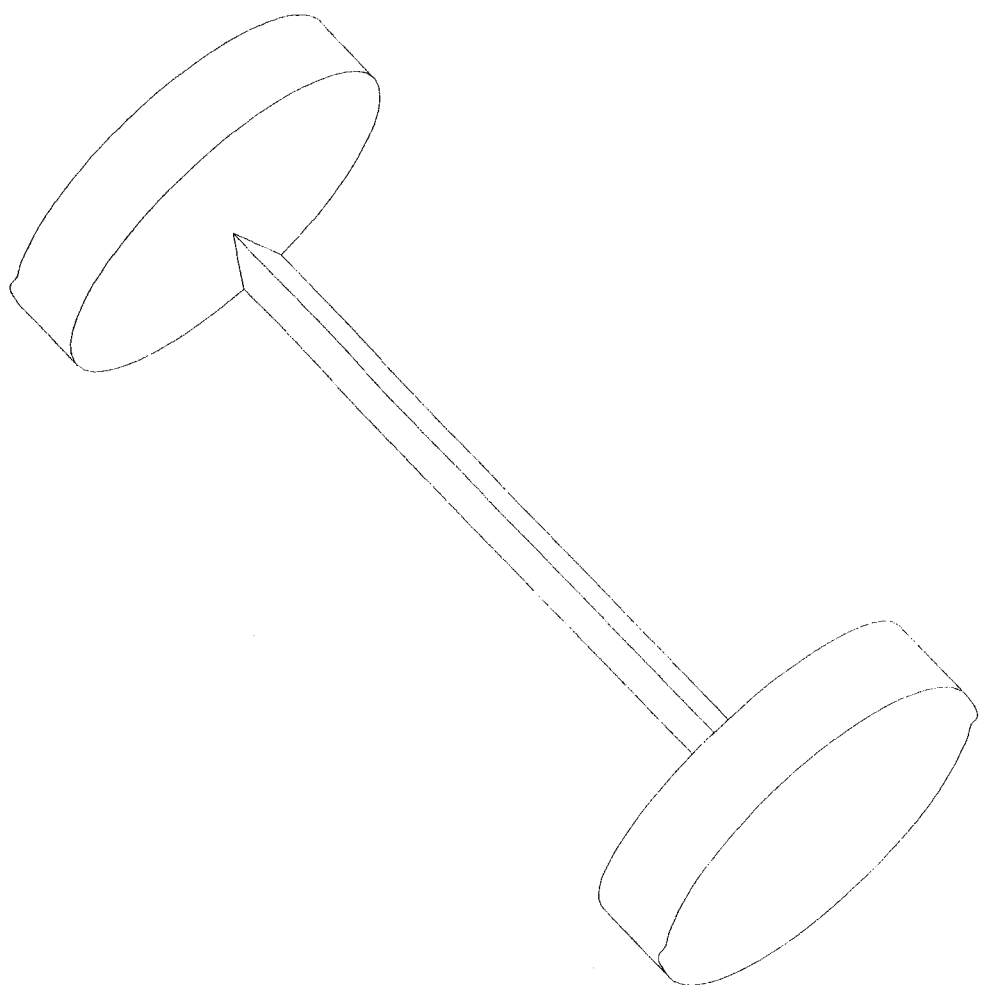
FIG. 6 is a diagram showing volume of the cylinder not sampled by beams with a straight gap.
Figure 7:
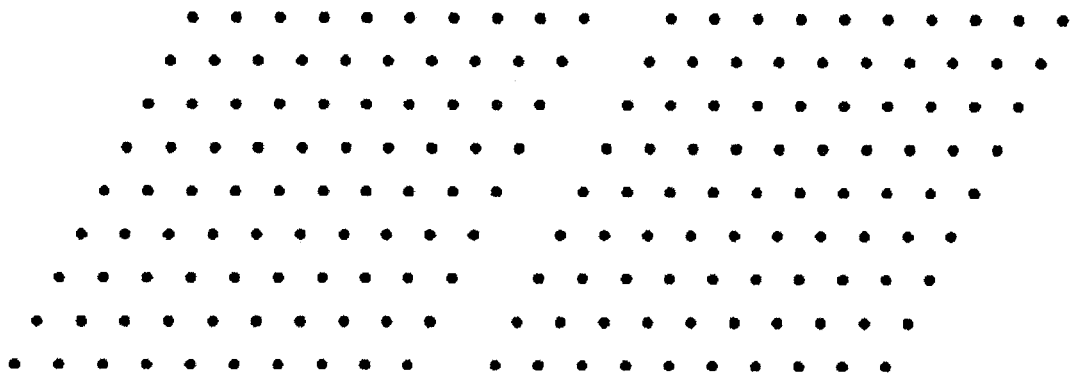
FIG. 7 is a diagram showing source positions with an angled gap between adjacent tubes or vacuum envelopes.
Figure 8:
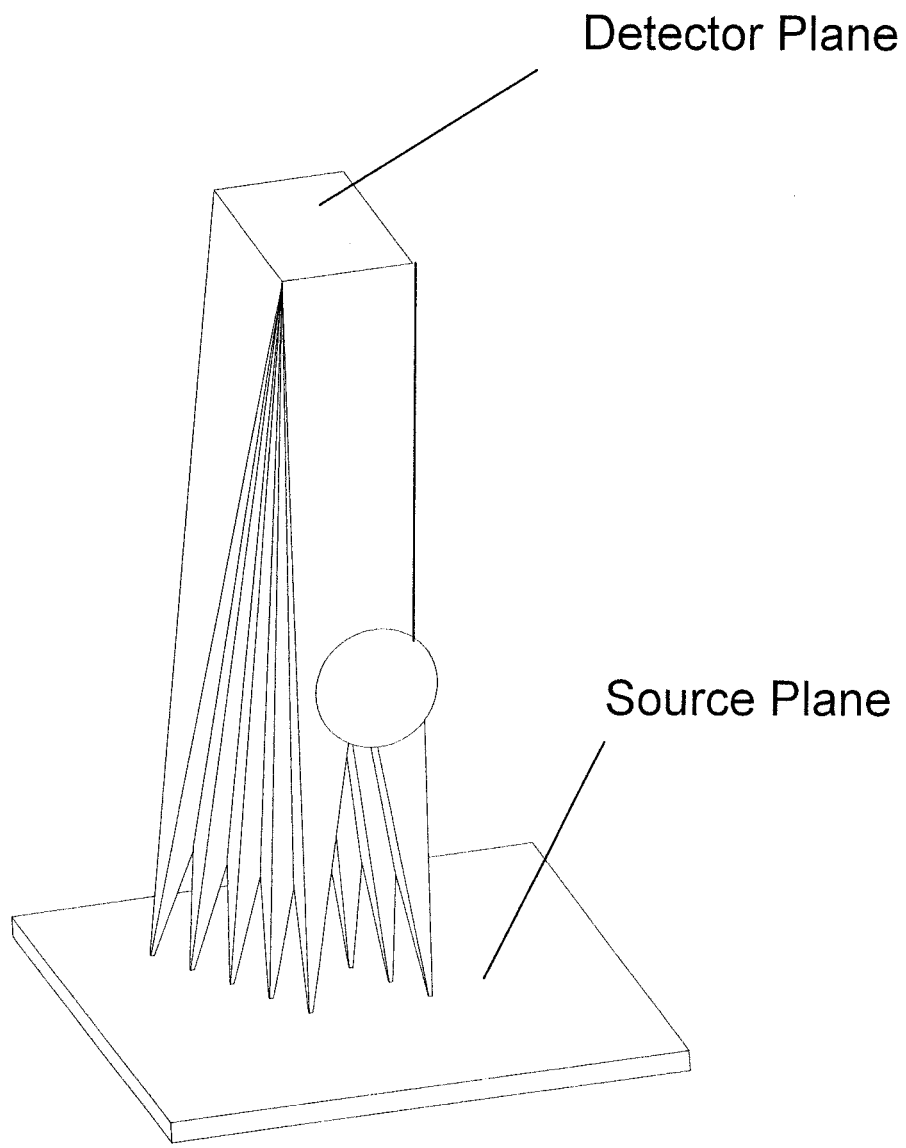
FIG. 8 is a diagram showing a cylinder penetrated by beams with an angled gap.
Figure 9:
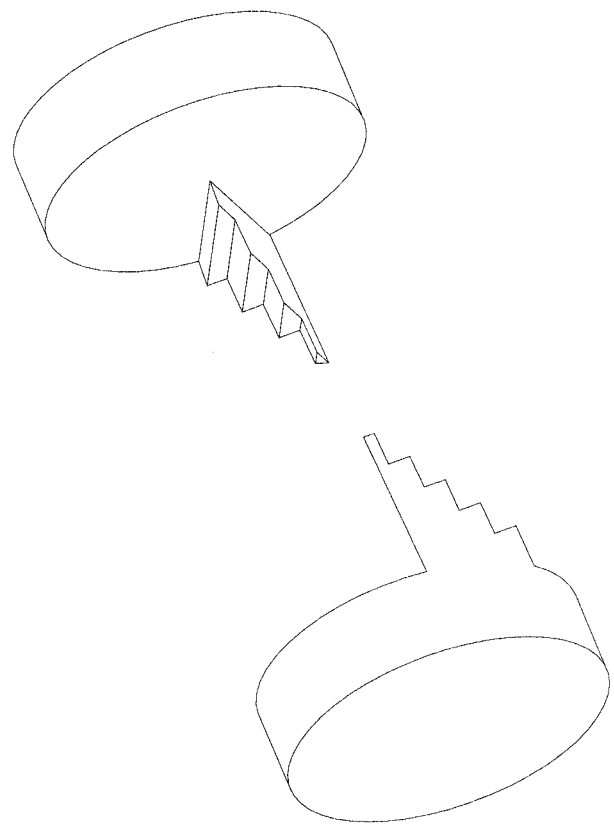
FIG. 9 is a diagram showing volume of the cylinder not sampled by beams with an angled gap.

FIG. 4 is a diagram showing source positions with a straight gap between adjacent tubes or vacuum envelopes. This approach has a straight gap parallel to the z-axis. FIG. 5 is a diagram showing a cylinder penetrated by beams with a straight gap. This figure shows how beams emitted from the source plane penetrate a homogeneous cylinder. FIG. 6 is a diagram showing volume of the cylinder not sampled by beams with a straight gap. The gap in the source plane leads to areas in the cylinder that are not sampled. Equivalently, there are regions of Radon space that have no data. FIG. 7 is a diagram showing source positions with an angled gap between adjacent tubes or vacuum envelopes. This approach has an angled gap that is not parallel to the z-axis. FIG. 8 is a diagram showing a cylinder penetrated by beams with an angled gap. FIG. 9 is a diagram showing volume of the cylinder not sampled by beams with an angled gap. The area not sampled is greatly reduced when the gaps are angled. Thus, complete sampling with a nine-gap configuration is feasible.

A more rigorous definition of sampling completeness is Tuy's criterion. A projection dataset is complete if any plane through the object being imaged also intersects the source trajectory. From Tuy's criterion, it is clear that two-dimensional fan-beam geometry produces a complete dataset. However, cone-beam geometry, where the source is on a circular trajectory, is incomplete. Planes through the object perpendicular to z do not intersect the source trajectory unless they coincide with the source plane. This gives rise to the cone-beam artifact in cone-beam CT.

Tuy's criterion assumes implicitly that a projection from any source position produces a complete image of the object. Thus, it is not very intuitive to apply Tuy's criterion where every given detector image is only a partial view of the object. However, with the assumption that the entire collimator is scanned before the detector moves more than a detector width, the following is true: From a given source spot, the detector is illuminated along an arc of the same length as the collimator. In other words, from a given source spot location, the detector is illuminated in a sequence of positions that sum up to a fan. At every source position, a complete image of the object is generated. Thus, Tuy's criterion can be applied.

Figure 10:
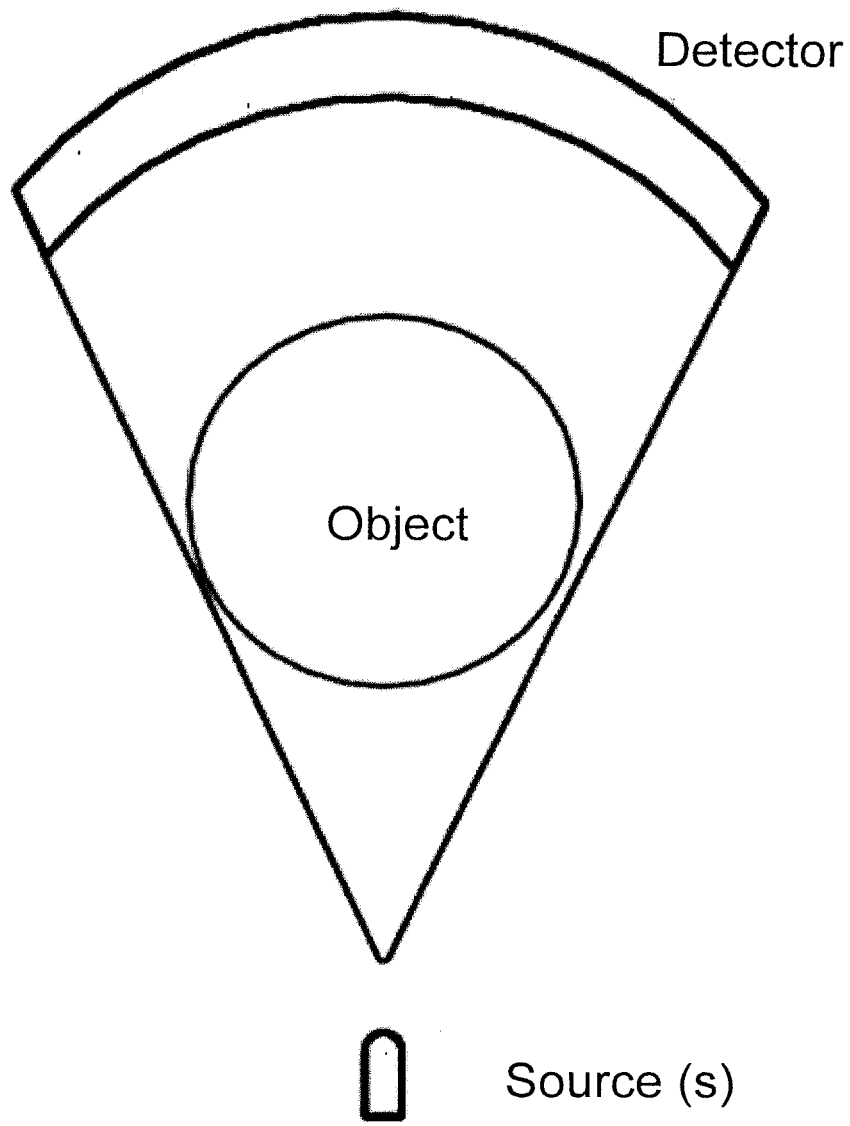
FIG. 10 is a diagram showing illumination by standard CT geometry.
Figure 11:
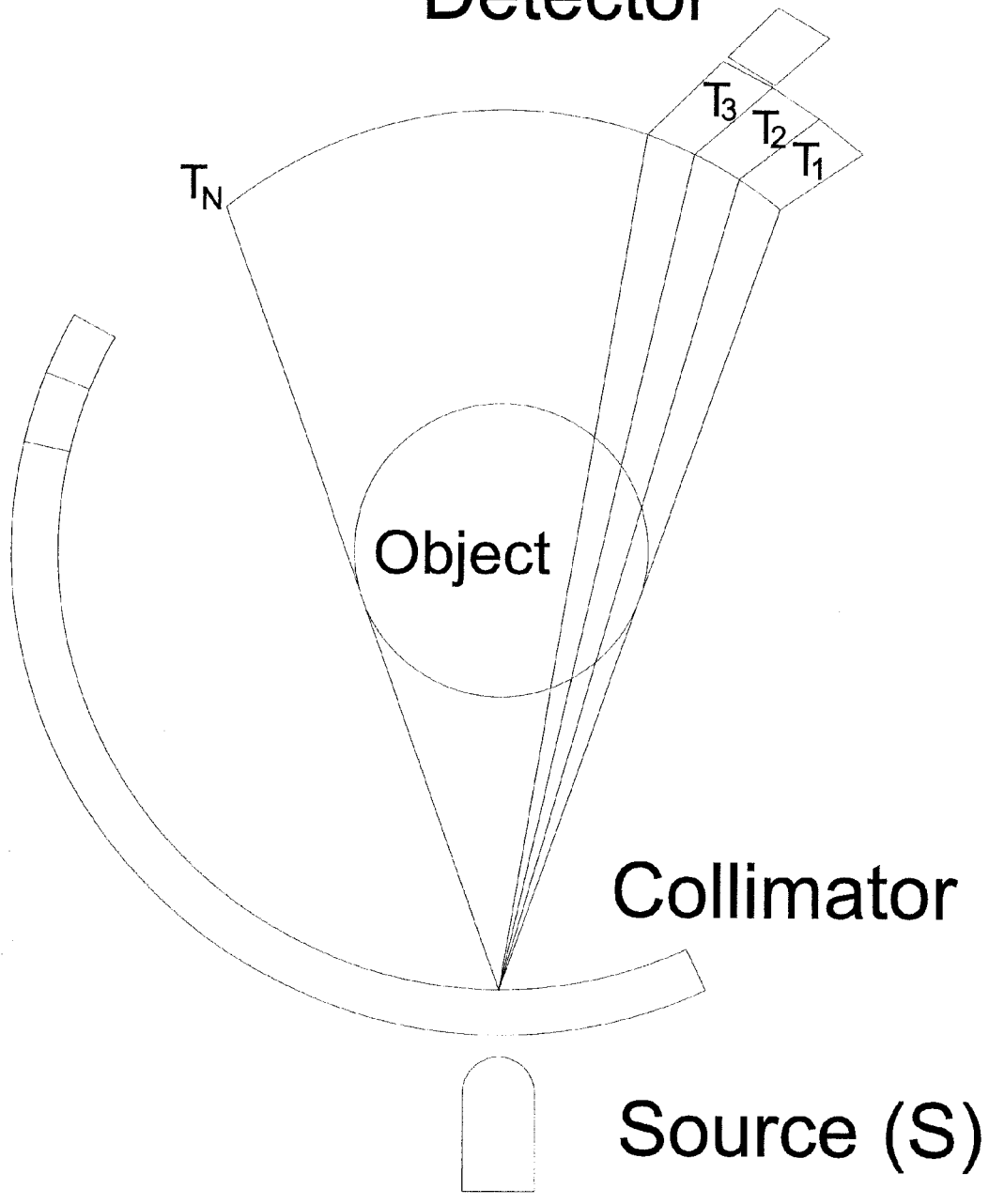
FIG. 11 is a diagram showing illumination by an exemplary computed tomography imaging system of one embodiment of the present invention.

FIG. 10 is a diagram showing illumination by standard CT geometry. At each source position, the entire object is illuminated and recorded by the detector. FIG. 11 is a diagram showing illumination by an exemplary computed tomography imaging system of one embodiment of the present invention. Multiple source positions project through the collimator. Only one source position (S) is examined. At time $T_1$ a small cone of the object is illuminated. The source spot is revisited at time $T_2$ after the collimator has moved a certain distance. Now the spot illuminates a different part of the object (dark cone). This continues as long as the collimator is in front of the given spot, until time $T_N$. After time $T_N$, the same cone has been illuminated thereby producing a complete view.

In the case of the three-gap system, application of Tuy's criterion reveals that an object is sampled completely within a circle inscribed in the triangle formed by the three gaps. For the angled nine-gap system, because all planes intersect a source, complete sampling is provided.

Figure 12:
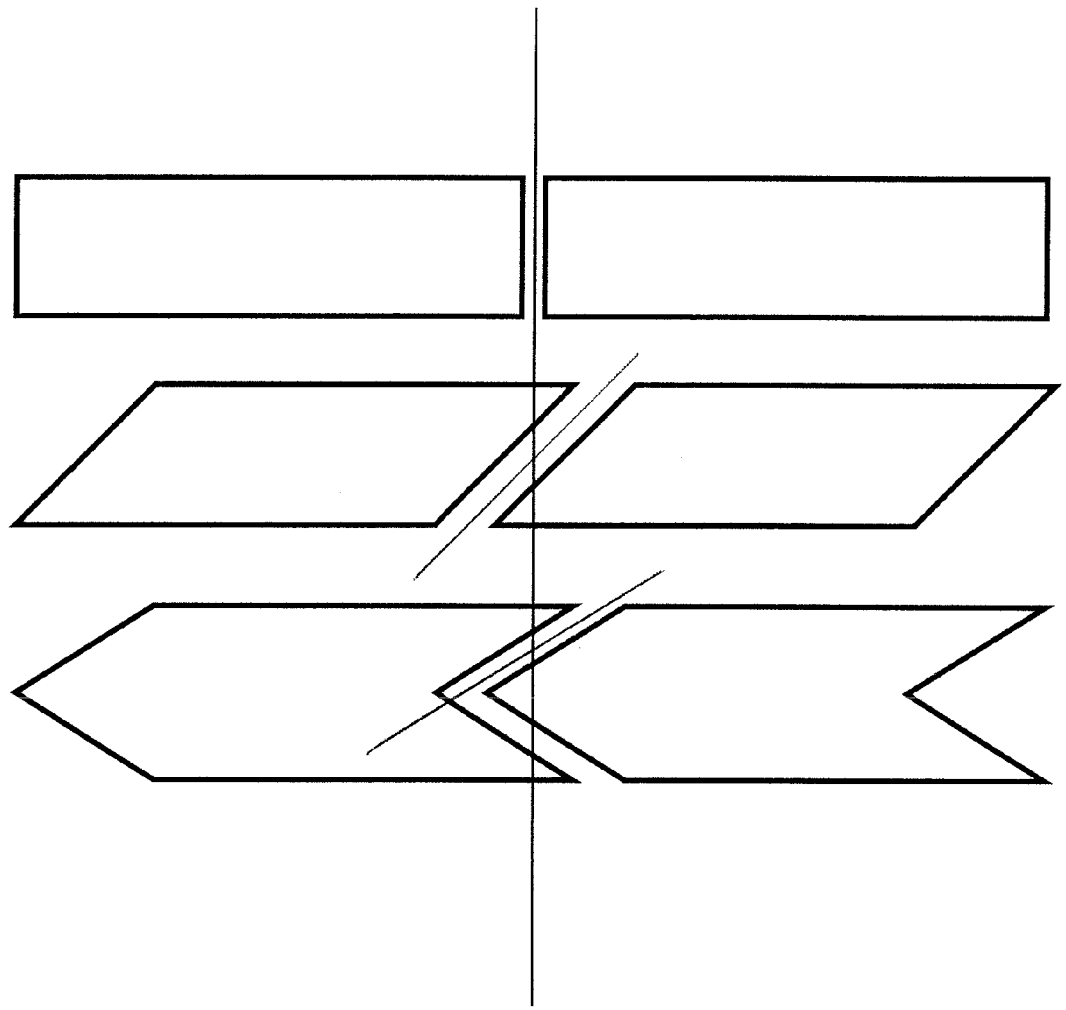
FIG. 12 is a diagram showing different shapes of gaps between adjacent X-ray source arrays of an exemplary computed tomography imaging system of one embodiment of the present invention.

FIG. 12 is a diagram showing different shapes of gaps between adjacent X-ray source arrays of an exemplary computed tomography imaging system of one embodiment of the present invention. The dotted lines indicate planes inserted in the imaging volume intersecting with the source array. The edge of the gap can be perpendicular to the long edge of the source array. In this case, the gap is a straight gap. The width of the gap measured between active portions of the source array can be 1, 5, 10, 15, 20 cm or any width in between such widths or any range of widths less than 20 cm. A plane can be inserted in the imaging volume without intersecting sources in the source array. Alternatively, the edge of the gap can be angled with respect to the long edge of the source array. The angle between the edge of the gap and the long edge of the source array can be 45 degrees but can also be any angle from 5 to 45 degrees. In this case, the gap is an angled gap. The width of the gap measured between active portions of the source array can be 1, 5, 10, 15, 20 cm or any width in between such widths or any range of widths less than 20 cm. In a complete 360 degree scan, opposite sources would be intersected. When the object is illuminated from all source positions in a full circle with an angled gap or 360 degree scan, all planes intersect a source and complete sampling is provided. But when the object is not illuminated from all source positions in a full circle, not all planes will intersect a source and complete sampling may not occur. To achieve complete sampling with partial illumination or illumination from source positions less than a full circle, a chevron shaped gap can be used as shown in FIG. 12. A chevron shaped gap cannot be intersected by a plane without intersecting sources. A chevron shaped gap does not rely on a complete rotation for sampling completeness. The angle between one edge of the gap and a long edge of the source array can be 135 degrees but can also be any angle from 112 to 157 degrees. The angle between the second edge of the gap and a long edge of the source array can be 135 degrees but can also be any angle from 112 to 157 degrees. The width of the gap measured between active portions of the source array can be 1, 5, 10, 15, 20 cm or any width in between such widths or any range of widths less than 20 cm. The height of a triangle formed by the chevron shaped gap can be greater than the width of the gap.

Figure 13:
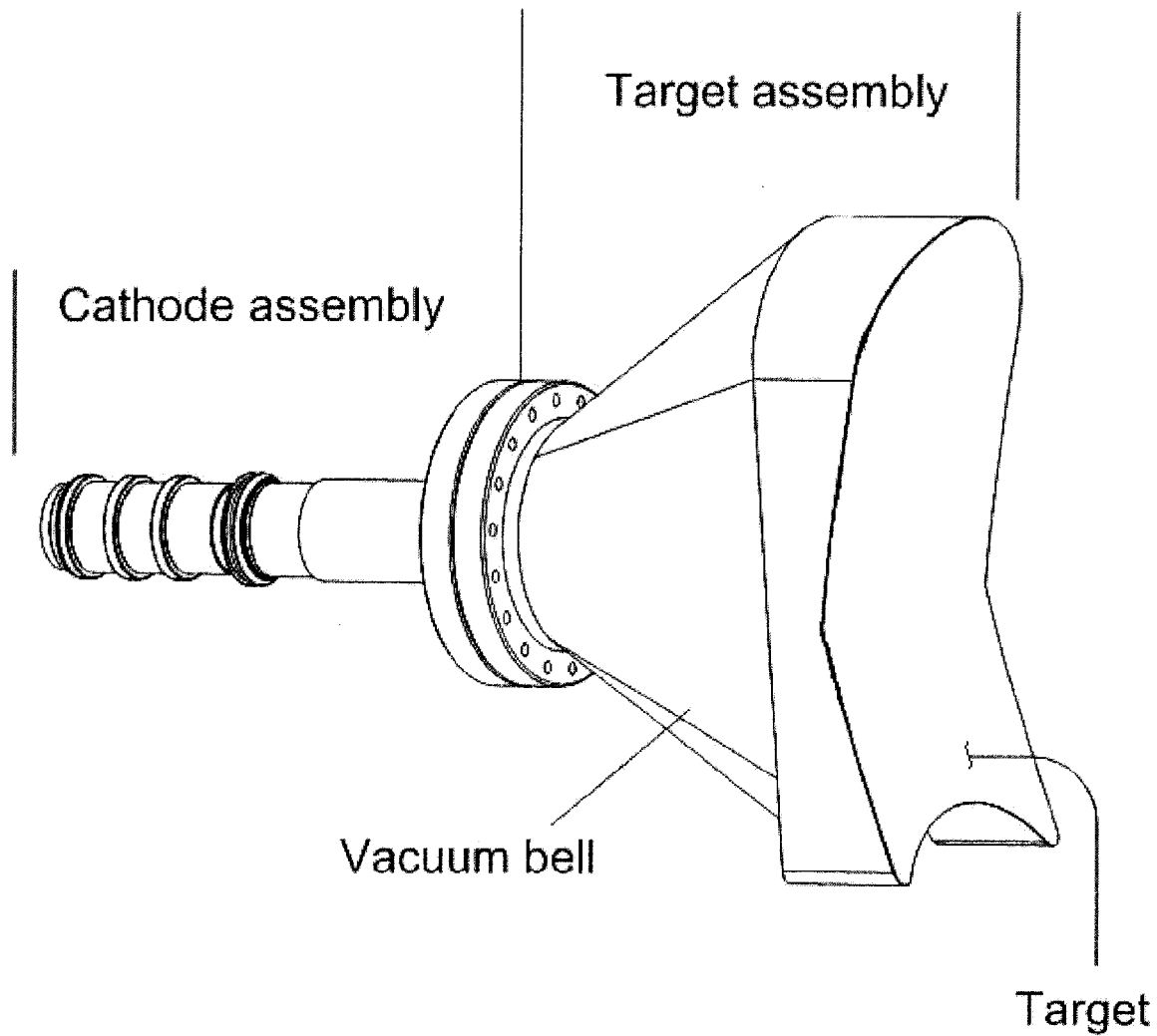
FIG. 13 is a diagram showing an X-ray tube with chevron shaped gap of an exemplary computed tomography imaging system of one embodiment of the present invention.

FIG. 13 is a diagram showing an X-ray tube with chevron shaped gap of an exemplary computed tomography imaging system of one embodiment of the present invention.

A virtual bowtie filter can be implemented. The object can be illuminated more where it is more opaque (thicker) and less where it is less opaque (thinner). Long path lengths can lead to high attenuation of the incident beam which, in turn, leads to low count rates. The majority of source positions can lead to count rates that are at least ten times higher than the lowest count rate. Using a virtual bowtie, acquisition times can be increased in areas of low count rates and decreased in areas with high count rates thereby equalizing the number of detected photons. In an ideal case the acquisition times of most source positions (90%) could be reduced to 10% of those in the low count rate areas. Acquisition time savings of a factor of four can be achieved. The bowtie filter can preserve the overall timing and angular sampling of the CT scan.

Figure 14:
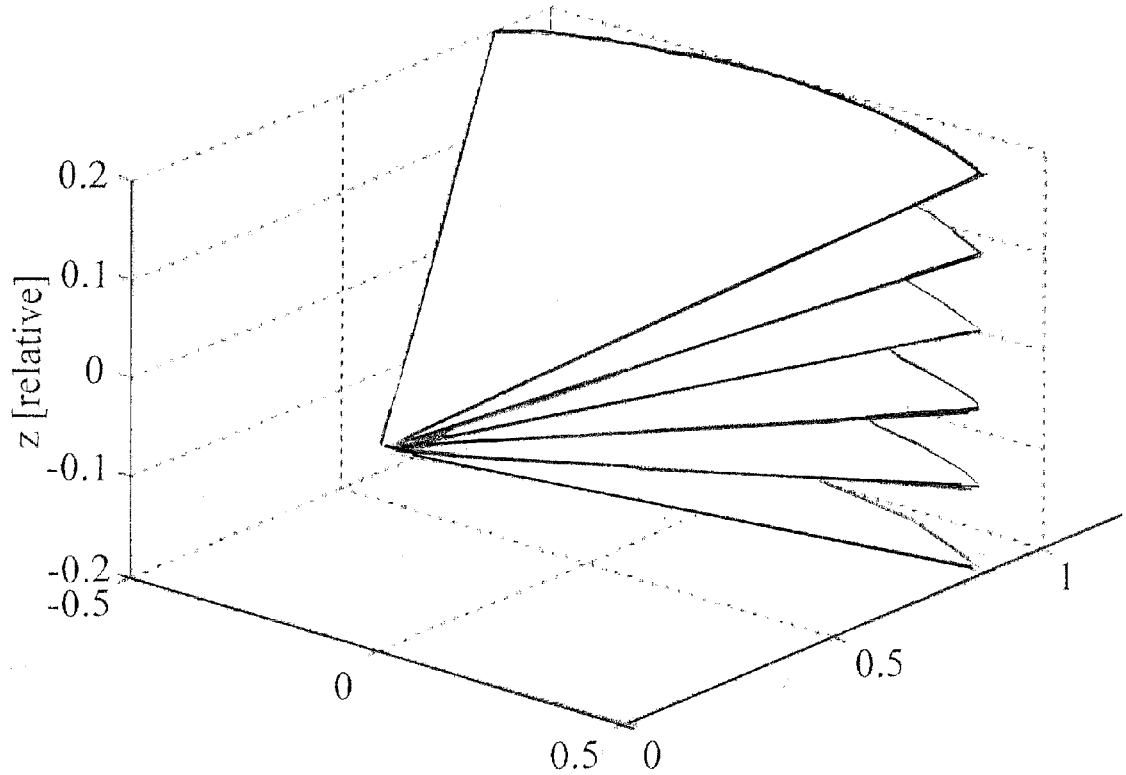
FIG. 14 is a diagram showing sampling planes corresponding to one source spot in the center of the source, and a number of rows of the detector extended by the rotation of the detector of FDK (Feldkamp) cone beam reconstruction algorithm of one embodiment of the present invention.

A variety of reconstruction algorithms can be used for reconstruction of the CT data. FIG. 14 is a diagram showing sampling planes corresponding to one source spot in the center of the source, and a number of rows of the detector extended by the rotation of the detector of FDK (Feldkamp) cone beam reconstruction algorithm of one embodiment of the present invention. The FDK algorithm, referred to as a "cone-beam" reconstruction algorithm can be used. In FIG. 14, each sector represents the data sampled by one source location illuminating one row of the detector as the detector rotates through the field of view. Only six such sampling sectors are shown, whereas the real detector would have, say, 160 such rows. The data represented in FIG. 14 constitute a cone-beam projection. The collection of data for all angular positions of the source spot constitutes a conventional cone-beam data set. For each of the other source rows, a similar cone-beam data set is acquired. Each of these can be reconstructed using FDK. The only issue with this approach is that one is reconstructing many of the same voxels from independent cone-beam data sets, producing largely redundant reconstructions.

Figure 15:
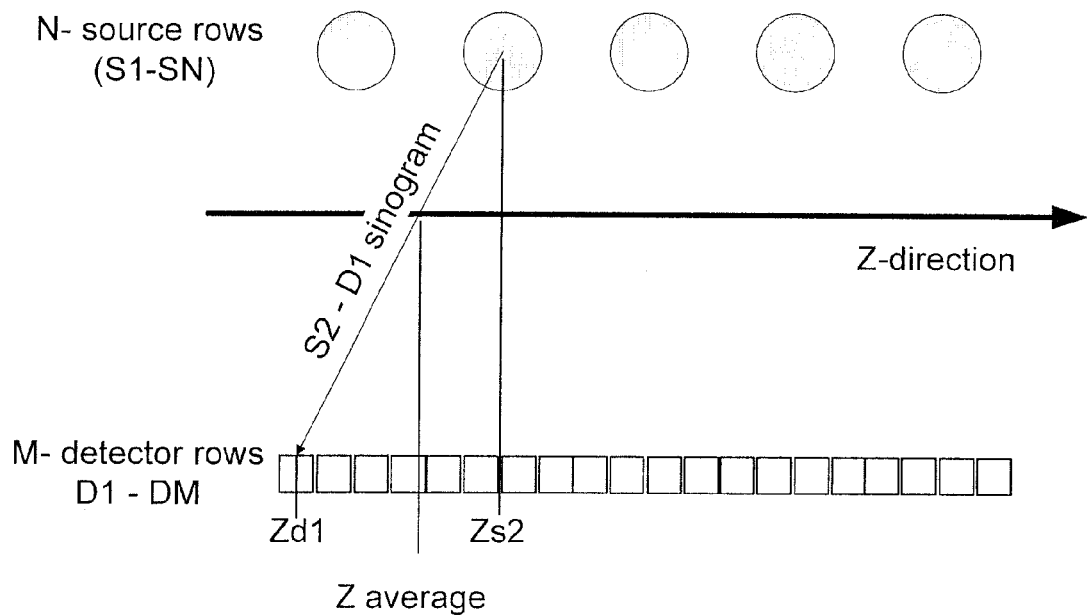
FIG. 15 is a diagram showing geometry and nomenclature for the FORE algorithm of one embodiment of the present invention producing N×M oblique sonograms.

FIG. 15 is a diagram showing geometry and nomenclature for the FORE algorithm of one embodiment of the present invention producing N×M oblique sonograms. The FORE algorithm provides a way to enforce consistency on the estimates of attenuation in the CT data set. In the CT geometry at every source location along the arc a detector image is formed. After completion of a rotation, the data from every detector row can be rebinned into sinograms. Further rebinning yields parallel ray oblique sinograms for every source row and detector row. This step is always possible if sampling is complete. For incomplete data this step will yield incomplete sinograms which can be compensated by the FORE algorithm.

Figure 16:
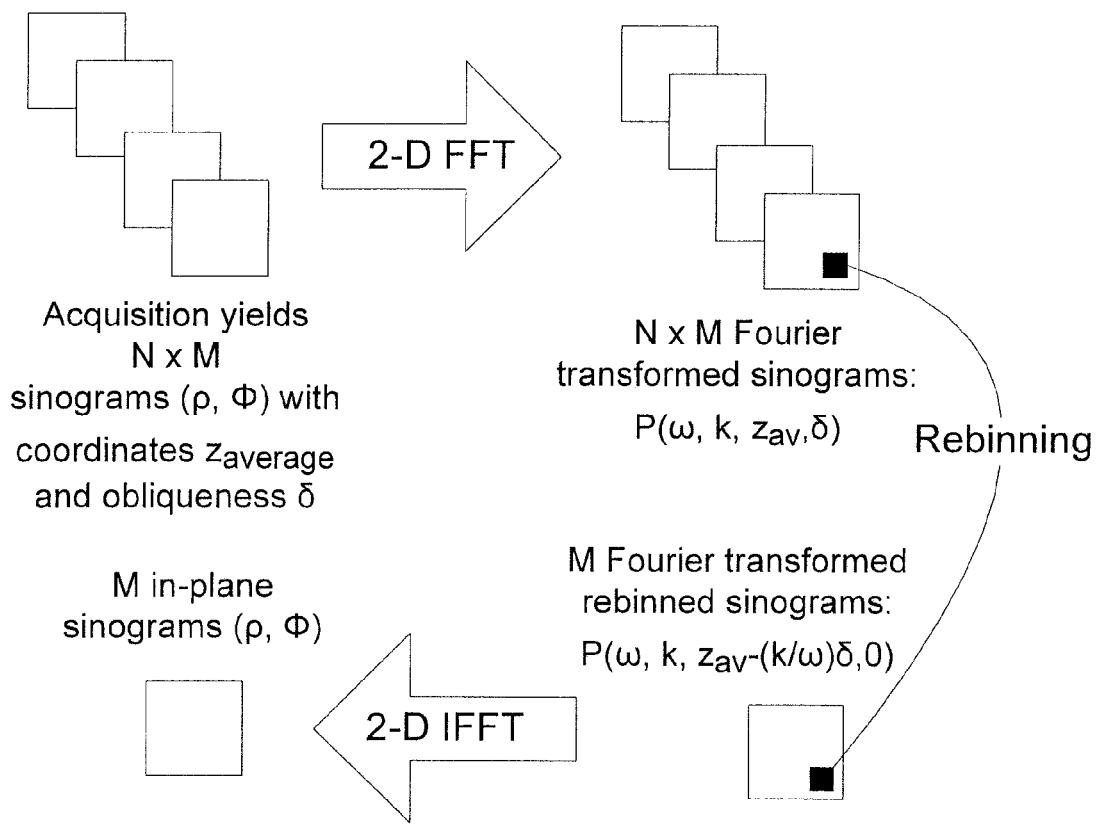
FIG. 16 is a flowchart diagram showing the FORE algorithm of one embodiment of the present invention.

FIG. 16 is a flowchart diagram showing the FORE algorithm of one embodiment of the present invention. The N×M oblique parallel ray sinograms are Fourier transformed yielding a four dimensional data set in the coordinates ($\omega$, k, zav, $\delta$). The next step is to rebin this dataset into a three-dimensional dataset with the coordinates ($\omega$, k, zav−(k/$\omega$)*$\delta$, 0) with the fourth coordinate of zero indicating in-plane datasets. Inverse Fourier transform yields a set of in-plane sinograms which can be reconstructed with filtered backprojection. Computer simulation using a Shepp-Logan phantom can be used. First, a complete dataset of parallel ray oblique sinograms can be calculated and reconstructed. Then views can be omitted in a way to simulate a dataset from a system with a straight gap and a system with angled gap. Results from the straight gap show a significant loss in image quality while the results from an angled gap show image quality comparable to the reconstruction from a complete dataset. These results show that a system with multiple gaps (greater than three) is possible. Filtered back projection approaches can be used.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A computed tomography x-ray imaging system for imaging a human patient comprising:

a plurality of x-ray sources for delivering x-ray radiation to said human patient;

a plurality of gaps of less than 20 cm between said x-ray sources;

a collimator located between said plurality of x-ray sources and said human patient for projecting said x-ray radiation through said human patient; and a x-ray detector for measuring amount of said x-ray radiation passing through said human patient and striking said detector.

2. The computed tomography x-ray imaging system of claim 1 wherein said gaps are angled.

3. The computed tomography x-ray imaging system of claim 1 wherein an angle between an edge of such gaps and a long edge of a source array of said sources is 45 degrees.

4. The computed tomography x-ray imaging system of claim 1 wherein an angle between an edge of such gaps and a long edge of a source array of said sources is between 5 and 45 degrees.

5. The computed tomography x-ray imaging system of claim 1 wherein said gaps are chevron shaped.

6. The computed tomography x-ray imaging system of claim 1 wherein an angle between one edge of said gaps and a long edge of a source array of said sources is 135 degrees.

7. The computed tomography x-ray imaging system of claim 5 wherein a height of a triangle formed by said chevron shaped gap is greater than a width of said gap.

* * * * *